United States Patent
Tsyrlova et al.

(10) Patent No.: US 9,428,552 B2
(45) Date of Patent: Aug. 30, 2016

(54) STEM CELL MOBILIZATION AND TISSUE REPAIR AND REGENERATION

(71) Applicant: Wellstat Therapeutics Corporation, Gaithersburg, MD (US)

(72) Inventors: Irena Tsyrlova, Bethesda, MD (US); Fawn Petty, Bowie, MD (US); Reid W. von Borstel, Potomac, MD (US); Julian Reading, Frederick, MD (US); Jiong Pei, Dobbs Ferry, NY (US); Joel Saydoff, Frederick, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 0 days.

(21) Appl. No.: 14/442,737

(22) PCT Filed: Nov. 18, 2013

(86) PCT No.: PCT/US2013/070560
§ 371 (c)(1),
(2) Date: May 14, 2015

(87) PCT Pub. No.: WO2014/078787
PCT Pub. Date: May 22, 2014

(65) Prior Publication Data
US 2016/0016997 A1    Jan. 21, 2016

Related U.S. Application Data

(60) Provisional application No. 61/735,227, filed on Dec. 10, 2012, provisional application No. 61/728,058, filed on Nov. 19, 2012.

(51) Int. Cl.
C07K 7/08    (2006.01)
A61K 38/00    (2006.01)

(52) U.S. Cl.
CPC .. *C07K 7/08* (2013.01); *A61K 38/00* (2013.01)

(58) Field of Classification Search
CPC .......................................................... C07K 7/08
USPC ................. 514/6.9, 21.5, 16.5, 113.3, 13.3
See application file for complete search history.

(56) References Cited

U.S. PATENT DOCUMENTS

| 5,114,926 | A | 5/1992 | Frindel et al. |
| 5,939,391 | A * | 8/1999 | Tsyrlova ............... A61K 38/42 514/13.5 |
| 6,610,654 | B2 * | 8/2003 | Tsyrlova ............... A61K 38/42 424/85.4 |
| 8,080,524 | B2 | 12/2011 | Bakala et al. |
| 2003/0104984 | A1 | 6/2003 | Tsyrlova et al. |
| 2007/0098680 | A1 | 5/2007 | Kawabe et al. |
| 2007/0259819 | A1 | 11/2007 | Bakala et al. |
| 2010/0041147 | A1 | 2/2010 | Tsyrlova et al. |
| 2011/0104175 | A1 | 5/2011 | Bernstein et al. |
| 2011/0172155 | A1 | 7/2011 | Crockford et al. |
| 2014/0088006 | A1 | 3/2014 | Tsyrlova et al. |
| 2015/0111238 | A1 * | 4/2015 | Tang .................. G01N 33/6848 435/23 |

FOREIGN PATENT DOCUMENTS

| WO | 9728183 A1 | 8/1997 |
| WO | 9736922 A1 | 10/1997 |
| WO | 2004091661 A1 | 10/2004 |
| WO | 2012159044 A1 | 11/2012 |

OTHER PUBLICATIONS

Machine translation of WO 2004/091661, pp. 1-8, Oct. 2004.*
UniProt Direct Submission P19104. Hemoglobin subunit alpha. Jan. 23, 2007. [Retrieved from the Internet Jan. 10, 2014: <http://www.uniprot.org/uniprot/P19104.txt?version=70>]; amino acids 43-55.
Azizi et al., "Acute Angiotensin-converting Enzyme Inhibition Increases the Plasma Level of the Natural Stem Cell Regulator N-Acetyl-Seryl-Aspartyl-Lysyl-Proline", J. Clin. Invest., 97(3): 839-844, Feb. 1996.
Myohanen et al., "Prolyl oligopeptidase induces angiogenesis both in vitro and in vivo in a novel regulatory manner", Br. J. Pharmacol., 163: 1666-1678, 2011.
Shen et al., "The peptide network regulated by angiotensin converting enzyme (ACE) in hematopoiesis", Cell Cycle, 10 (9): 1363-1369, 2011. <http://dx.doi.org/10.4161/cc.10,9.15444>.
Claims in Application No. 14/118,313 as amended Nov. 23, 2015.

* cited by examiner

*Primary Examiner* — Julie Ha
(74) *Attorney, Agent, or Firm* — Lewis J. Kreisler

(57) ABSTRACT

Stem cells are mobilized from bone marrow by administering an amount of Phe-Pro-His-Phe-Asp-Leu-Ser-His-Gly-Ser-Ala-Gln-Val-Ser-Asp-Lys-Pro (SEQ ID NO: 2) or Phe-Ala-His-Phe-Asp-Leu-Ser-His-Gly-Ser-Ala-Gln-Val-Ser-Asp-Lys-Pro (SEQ ID NO: 3) effective to mobilize the stem cells. This is useful for promoting bodily tissue regeneration in a patient in need of tissue regeneration treatment. Alternatively, the mobilized stem cells can be collected for transplant.

18 Claims, 16 Drawing Sheets

A. Matrigel Plug with PBS    B. Matrigel Plug with bFGF

A. Matrigel plug, containing bFGF in C57Bl6 mouse Day 9

B. Matrigel plug, containing bFGF in db/db mouse Day 13

```
                       SEQUENCE LISTING

<160> NUMBER OF SEQ ID NOS: 7

<210> SEQ ID NO 1
<211> LENGTH: 17
<212> TYPE: PRT
<213> ORGANISM: Artificial Sequence
<220> FEATURE:
<223> OTHER INFORMATION: sequence is synthesized
<220> FEATURE:
<221> NAME/KEY: MISC_FEATURE
<222> LOCATION: 2..2
<223> OTHER INFORMATION: Xaa = Pro or Ala

<400> SEQUENCE: 1

Phe Xaa His Phe Asp Leu Ser His Gly Ser Ala Gln Val Ser Asp Lys
1               5                   10                  15

Pro

<210> SEQ ID NO 2
<211> LENGTH: 17
<212> TYPE: PRT
<213> ORGANISM: Artificial Sequence
<220> FEATURE:
<223> OTHER INFORMATION: sequence is synthesized

<400> SEQUENCE: 2

Phe Pro His Phe Asp Leu Ser His Gly Ser Ala Gln Val Ser Asp Lys
1               5                   10                  15

Pro

<210> SEQ ID NO 3
<211> LENGTH: 17
<212> TYPE: PRT
<213> ORGANISM: Artificial Sequence
<220> FEATURE:
<223> OTHER INFORMATION: sequence is synthesized

<400> SEQUENCE: 3

Phe Ala His Phe Asp Leu Ser His Gly Ser Ala Gln Val Ser Asp Lys
1               5                   10                  15

Pro

<210> SEQ ID NO 4
<211> LENGTH: 13
<212> TYPE: PRT
<213> ORGANISM: Artificial sequence
<220> FEATURE:
<223> OTHER INFORMATION: sequence is synthesized

<400> SEQUENCE: 4
```

```
Phe Pro His Phe Asp Leu Ser His Gly Ser Ala Gln Val
1               5                   10

<210> SEQ ID NO 5
<211> LENGTH: 4
<212> TYPE: PRT
<213> ORGANISM: Artificial sequence
<220> FEATURE:
<223> OTHER INFORMATION: sequence is synthesized
<220> FEATURE:
<221> NAME/KEY: ACETYLATION
<222> LOCATION: (1)..(1)
<223> OTHER INFORMATION: N-acetyl

<400> SEQUENCE: 5

Ser Asp Lys Pro
1

<210> SEQ ID NO 6
<211> LENGTH: 15
<212> TYPE: PRT
<213> ORGANISM: Artificial sequence
<220> FEATURE:
<223> OTHER INFORMATION: sequence is synthesized

<400> SEQUENCE: 6

His Phe Asp Leu Ser His Gly Ser Ala Gln Val Ser Asp Lys Pro
1               5                   10                  15

<210> SEQ ID NO 7
<211> LENGTH: 14
<212> TYPE: PRT
<213> ORGANISM: Artificial sequence
<220> FEATURE:
<223> OTHER INFORMATION: sequence is synthesized

<400> SEQUENCE: 7

Phe Asp Leu Ser His Gly Ser Ala Gln Val Ser Asp Lys Pro
1               5                   10
```

STEM CELL MOBILIZATION AND TISSUE REPAIR AND REGENERATION

BACKGROUND OF THE INVENTION

Adult tissue stem cells including hematopoietic stem cells (HSC) are unique and rare cells responsible for regeneration of different tissues: blood, muscles, hair follicles, skin keratinocytes, pancreatic and neural cells (Orlic et al. 2001, Krause et al. 2001). Stem cell transplantation has been tested in clinical trials for tissue regeneration with a various but low degree of success. This is due to the fact that even after enrichment with the most up-to-date approaches, the resulting HSC populations are not homogeneous. A large proportion of cells may still have no HSC potential, molecular heterogeneity within different HSC subsets and other uncertainties make cell transplantation less feasible for tissue regeneration than HSC mobilization.

Primitive stem cells exhibit differential motility responses to the chemokine, stromal derived factor-1 (SDF-1) and lysophospholipid mediator sphingosine-1-phosphate (S1P) recently found to play a critical role in stem cell mobilization. Mobilization of stem cells from bone marrow into peripheral blood prior to harvesting is currently being used in clinical settings of allogeneic stem cell transplantation instead of bone marrow. The most common mobilizing agent for clinical uses is granulocyte colony stimulating factor (G-CSF). Other molecules have mobilizing effect on bone marrow cells (AMD3100, IL8, GM-CSF and others) their effect is shown to be indirect and not stem cell specific.

G-CSF, for example, acts on mature bone marrow cells; cells release proteases cleaving the adhesion factors responsible for the retention of cells in bone marrow. AMD3100, the CXCR4 inhibitor, approved recently for stem cell mobilization induces a more specific mobilization of cells into the circulation than G-CSF via disruption of the CXCR4-SDF1 interaction of bone marrow cells with their microenvironment; not only stem cells, but their immature progenitors and even malignant cells in Multiple Myeloma and Acute Promyelocytic leukemia express CXCR4 and therefore migrate into peripheral blood. (Kareem, et al. 2009).

Thus, all current drugs affect multiple cell populations, releasing into circulation high numbers of cells and causing changes in the bone marrow microenvironment. Therefore, these approaches cannot be used for multiple rounds of stem cell mobilization for tissue regeneration. Furthermore, both G-CSF and AMD3100, while mobilizing cells that can promote tissue repair, can also impair homing of mobilized stem and progenitor cells to sites of tissue damage, AMD3100 by blocking CXCR4 (Dai et al., 2010), the receptor for SDF-1, a primary chemotactic factor released by injured tissues, and G-CSF by cleaving CXCR4 (Honold, et al., 2006).

Under homeostatic conditions many physiological mechanisms including stem cell mobilization are found to be controlled by circadian oscillations; maximal mobilization of HSC into blood stream was found in mice at 5 hr after the onset of light with a reversed circadian HSC mobilization time (early night) demonstrated for human (Lucas, et al. 2008).

A stem-cell-specific mechanism increasing physiological level of cell mobilization is required for tissue regeneration and a drug that can be applied for multiple rounds of mobilization i.e. repeatedly causing stem cell egress from bone marrow without side effects and without impairing CXCR4-mediated homing of mobilized cells to damaged tissues is needed.

SUMMARY OF THE INVENTION

This invention provides an oligopeptide having the sequence Phe-Xaa-His-Phe-Asp-Leu-Ser-His-Gly-Ser-Ala-Gln-Val-Ser-Asp-Lys-Pro (SEQ ID NO: 1), wherein Xaa is Pro or Ala. This invention provides a method of mobilizing stem cells from bone marrow of a subject, comprising administering to the subject an amount of (SEQ ID NO: 1) effective to mobilize the stem cells. This method is useful for promoting bodily tissue regeneration in a patient in need of tissue regeneration treatment. Alternatively, the mobilized stem cells can be collected for transplant. It behaves as bidirectional regulator of hematopoietic cell growth, the effects is being dependent on both differentiation status and the presence of serum and some cytokines like SCF, IL3 and FGF among others. In contrast to other growth suppressor molecules such as macrophage inflammatory protein-1α (MIP-1α) or TGF-β1 the growth-inhibitory effects of the peptide is not apparent throughout the whole stem cell hierarchy, but only on the very primitive long term repopulating cells (LTRCs) engrafting cobblestone forming cells (CAFC), SCID repopulating cells (SRC) and colony forming cells (CFU-GEMM). The invention also features a method of modulating apoptosis in a cell able to form colony containing all types of hematopoietic cells.

DETAILED DESCRIPTION OF THE INVENTION

Figure 1:
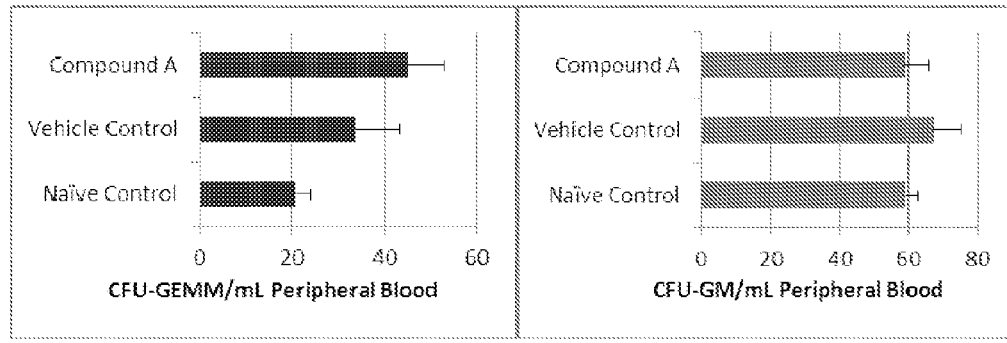
FIG. 1. Number of early HSC-CFU-GEMM and their progenitors CFU-GM 1 hr after subcutaneous injection of Compound A.

In separate embodiments of this invention the oligopeptide of this invention has the sequence Phe-Pro-His-Phe-Asp-Leu-Ser-His-Gly-Ser-Ala-Gln-Val-Ser-Asp-Lys-Pro (SEQ ID NO: 2) (also referred to as Compound A) or Phe-Ala-His-Phe-Asp-Leu-Ser-His-Gly-Ser-Ala-Gln-Val-Ser-Asp-Lys-Pro (SEQ ID NO: 3) (also referred to as Compound B). Some of the examples refer to an oligopeptide having the sequence Phe-Pro-His-Phe-Asp-Leu-Ser-His-Gly-Ser-Ala-Gln-Val (SEQ ID NO: 4) (also referred to as Compound C), which is included for comparison with the oligopeptides of this invention. N-acetyl-Ser-Asp-Lys-Pro (SEQ ID NO: 5) (also referred to as AcSDKP) was used as a control in some of the examples, as indicated. Example 8 refers to two truncated forms of Compound A, as follows: HFDLSHGSAQVSDKP (SEQ ID NO: 6) and FDLSHGSAQVSDKP (SEQ ID NO: 7).

Stem cells are mobilized from the bone marrow by a stem cell-stimulatory amount of (SEQ ID NO:1, 2 or 3). In humans, the appropriate amount of (SEQ ID NO: 1, 2, or 3) is generally from about 100 micrograms to about 1 milligram per day for one or more days. For example, the amount can be administered on each of four consecutive days. Typical amounts are, for example, 100 micrograms, 300 micrograms, 500 micrograms, or 1 milligram per day. Thus, in more specific embodiments of this invention, the ranges are from 90 to 110 micrograms, from 280 to 320 micrograms, from 450 to 550 micrograms, or from 900 to 1100 micrograms per day. (If too little is administered, the stem cells may be inhibited rather than stimulated, and mobilization may not occur. Inhibitory doses to be avoided are typically in the range of 50 ng to 1 microgram per day in a human.) Injection, for example subcutaneous injection, is the preferred route of administration. In accordance with this invention, bodily tissues generally can be regenerated. In one embodiment, pancreatic tissue is regenerated.

Most end-stage cells in renewing organs are short-lived and must be replaced continuously throughout life. The constant repopulation of renewing organs is driven by a group of undifferentiated cells called stem cells. Stem cells have the unique characteristic of being able to divide and to give rise to more differentiated progenitor cells ("differentiation") as well as to other stem cells ("self-renewal"). The ability to self-renew ensures that the population of stem cells is not depleted. Rapidly renewing tissues where stem cells have classically been demonstrated include hematopoietic tissue, skin, stomach, intestine, and testes.

Stem cells may be classified according to their differentiation potential as totipotent, pluripotent or multipotent. Totipotent stem cells are capable of forming any tissue in the body. The best example of this is the fertilized egg, which gives rise to both the embryo proper as well as the placenta and supporting tissues. Pluripotent stem cells can form a large subset of body tissues that can include most or all the tissues in the adult whereas multipotent stem cells have a more restricted repertoire of differentiation. Tissue progenitor cells are stem cells that can only differentiate into the cells that constitute a particular type of tissue.

Stem cells can produce new cells to repair damage to tissues and therefore have great potential for regenerative medicine. However, they exist in small quantities in tissues and especially in peripheral blood, making it difficult to collect them or use them clinically. To increase percentage of stem cells and their progenitors in peripheral blood, their mobilization by G-CSF prior to harvest has been used extensively. Mobilized stem cells can repair tissues if their homing and engraftment functions are not impaired (Rafii & Lyden, 2003). There is a need, therefore, to identify compounds that regulate mobilization of pluripotent stem cells and methods of uses for therapeutic purposes The chemokine, stromal cell-derived factor-1 (SDF-1/CXCL12), which binds and activates CXCR4 receptor, has been implicated as important mechanism for retention of stem cells within bone marrow microenvironment and mobilization into peripheral blood. AMD3100, a specific antagonist of SDF-1/CXCL12 binding to CXCR4, has been clinically tested and approved for synergizing with granulocyte colony-stimulating factor (G-CSF) to greatly enhance G-CSF-induced mobilization of HSCs/HPCs (Lapidot, T. and I. Petit. 2002, Lapidot et al., 2005).

CD26 is a cell-surface protein, which is a dipeptidylpeptidase IV (DPPIV) and has the capacity to truncate SDF-1/CXCL (De Meester et al., 1999). Human DPPIV is a 110 kDa cell surface molecule it contains intrinsic dipeptidyl peptidase IV activity, which selectively removes N-terminal dipeptide from peptides with proline or alanine in the third amino acid position. It interacts with various extracellular molecules and is also involved in intracellular signal transduction cascades. The multifunctional activities of human DPPIV are dependent on cell type and intracellular or extracellular conditions that influence its role as a proteolytic enzyme, cell surface receptor, co-stimulatory interacting protein and signal transduction mediator. Human DPPIV has a short cytoplasmatic domain from amino acid position 1 to 6, a transmembrane region from amino acid position 7 to 28, and an extracellular domain from amino acid position 29 to 766 with intrinsic DPPIV activity.

DPPIV-deficient mice exhibit resistance to diet-induced obesity, reduced fat accumulation, decreased plasma levels of leptin, increased pain sensitivity, reduced stress-like responses. DPPIV has been implicated in the control of lymphocyte and immune function, cell migration, viral entry, cancer metastasis, and inflammation; deletion of CD26 resulted in decreased mobilization of HPCs in response to exogenous administration of G-CSF (reviewed in Broxmeier et al. 2007).

DPPIV also regulates migration of human cord blood CD34+ progenitor cells and the homing and engraftment of hematopoietic stem cells. Inhibition of DPP-4 enzymatic activity promotes human hematopoietic stem cell migration and bone marrow engraftment via potentiation of the levels of intact CXCL12/SDF-1α, a physiological substrate for DPP-4 activity (Christopherson e.a 2002 and 2003).

The invention will be better understood by reference to the following examples, which illustrate but do not limit the invention described herein.

EXAMPLES

Example 1

Mobilization of Mouse Stem Cells from Bone Marrow into Peripheral Blood After Single Subcutaneous Injection of Compound A

Stimulatory doses of Compound A activate quiescent stem cells, induce them to proliferate and egress from bone marrow into peripheral blood. This example shows that an increase in number of hematopoietic stem cells (HSC) and their hematopoietic progenitors (HPC) measured by colony-forming assay happens within 1 hr after injection of stimulatory dose of Compound A and causes no changes in either cell number or cell composition. DBA/2J male mice (Jackson Laboratories) were subcutaneously injected with 0.9% saline (vehicle control) or 250 μg/kg of Compound A.

After 1 hour, mice were anesthetized and blood was collected through the orbital sinus with heparinized capillary tubes. To enumerate HSC and HPC in peripheral blood, cells were washed, counted and plated in semi-solid Methylcellulose (Stem cell technology) at 100,000 per dish (5 dishes/group) and placed in $CO_2$ incubator at 37° C. Colony-forming unit-granulocyte macrophage erythroid megakaryocyte (CFU-GEMM) and Colony-forming unit-granulocyte macrophage (CFU-GM) were detected under inverted microscope after 7-10 days in culture. Data presented in Tables 1, and FIG. 1.

TABLE 1

Colony-forming cell number in peripheral blood of mice 1 hr after subcutaneous injection of Compound A or Saline

| Treatment | CFU-GM/ 100000 cells | | CFU-GEMM/ 100000 cells | |
|---|---|---|---|---|
| | Mean | SE | Mean | SE |
| Naïve Control | 7.4 | 0.40 | 2.6 | 0.89 |
| Saline Control | 5.6 | 0.68 | 2.8 | 1.79 |
| Compound A | 11.8 | 1.36 | 9 | 3.54 |

White blood cell count (WBC) differs in different strains of mice, Compound A injection did not change WBC compared to Naïve or vehicle injected mice of the same strain while stem cell number in blood was increased 1 hr after 250 μg/kg dose of Compound A (FIG. 1). Thus, Compound A was able to increase CFU-GEMM number in blood very rapidly during 1 hr after injection, number of HSC per ml of blood increased 2.2 times compared to naïve mice.

Figure 2:
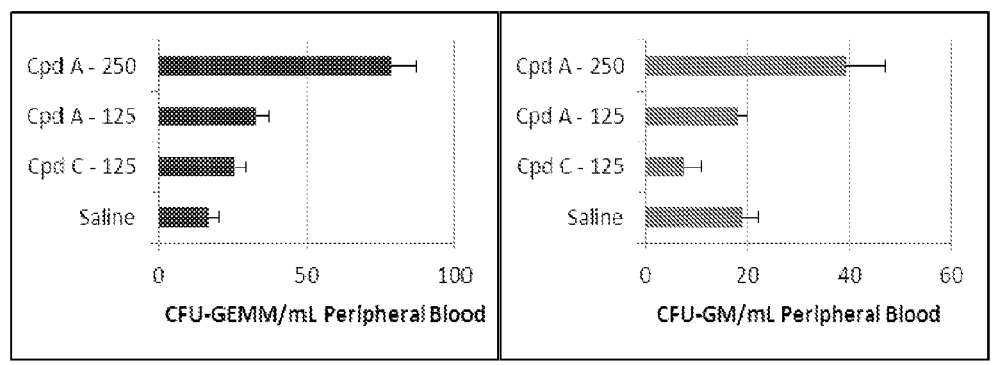
FIG. 2. Mobilization of CFU-GM and CFU-GEMM into peripheral blood 1 hr after single subcutaneous injection of Compound A.

Different doses of Compound A were tested from 50 μg/kg up to 5 mg/kg with mobilizing activity found only between doses 50-750 μg/kg. Of interest that Compound A effect on HSC and HPC was not accompanied by mobilization of other cells as far as cell number and phenotypes of cells in peripheral blood were not affected. COMPOUND A effect after single subcutaneous injection was compared with another active mobilizing peptide (FIG. 2) in that experiment Compound A was more active. The data indicates that both peptides induced mobilization of progenitor cells from the bone marrow into the peripheral blood of DBA/2J mice. A single 125 μg/kg dose mobilizes cells within one hour of administration at which time approximately a two-fold (Compound C) and four-fold (Compound A) increase in CFU-GEMM numbers was observed.

G-CSF or IL8 are known to have delayed effect on mobilization based on indirect mechanism of induced protease stimulation, Compound A mobilizing effect is fast (just one hour after injection) and stem cell specific.

AMD3100-CXCR4 receptor antagonist has fast mobilizing effect and works via Stromal-Derived Factor-1/CXCL12 mediated migration and homing unlike Compound A it stimulates not only primitive HSC but more mature progenitors like CFU-GM.

Example 2

Mobilization of Mouse Stem Cells from Bone Marrow into Peripheral Blood after Multiple Subcutaneous Injection of Compound A

The low levels of circulating HSPC are drastically increased in response to repeated stimulation with the cytokine G-CSF. This example is based on a protocol for a 5-day course of once-daily Compound A injections into DBA male mice similar to a G-CSF. An effective dose of Compound A was found previously to mobilize HSC 1 hr after single injection and was selected for this experiment.

DBA/2J male mice (Jackson Laboratories) were subcutaneously injected with 0.9% saline (vehicle control), 250 μg/kg Compound A (ThinkPeptides) for 5 consecutive days. At 7 days post initial injection, peripheral blood from 3 mice per group was harvested from the orbital plexus using capillary tubes (VWR) and collected into EDTA-containing tubes (VWR). Blood was also harvested and pooled from 3 naïve mice to serve as a naïve control group.

TABLE 2

Total number of CFU-GEMM and CFU-GM in peripheral blood of mice after multiple subcutaneous injections of Compound A.

| Treatment | CFU-GM/ 100000 cells | | CFU-GEMM/ 100000 cells | |
|---|---|---|---|---|
| | Mean | SE | Mean | SE |
| Naïve Control | 6.6 | 0.71 | 2.2 | 0.86 |
| Saline Control | 8 | 0.95 | 3.2 | 0.49 |
| Compound A | 11 | 1.4 | 7.6 | 0.24 |

Figure 3:
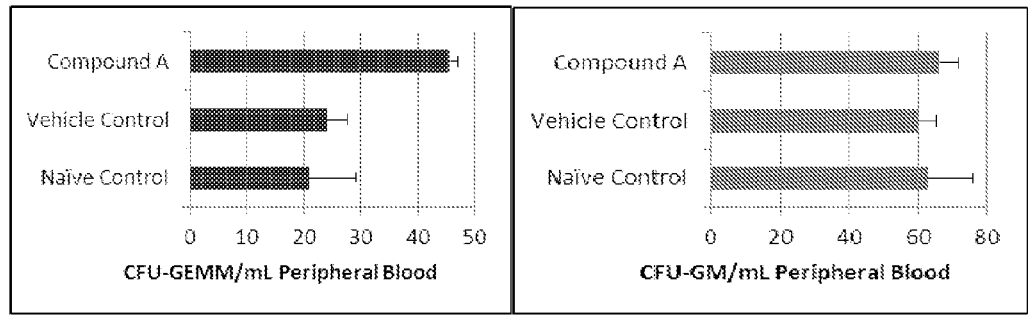
FIG. 3. Mobilization of CFU-GEMM and CFU-GM after multiple subcutaneous injections of Compound A.

Contrary to AMD3100, which induced an increase in white blood counts and a substantial increase in number of circulating precursors of granulocytes and macrophages—CFU-GM the injection of Compound A did not change the number of white blood cells and CFU-GM in peripheral blood of mice. Compound A increased CFU-GEMM number 2.2 times at dose 250 μg/kg (Table 2; FIG. 3).

Figure 4:
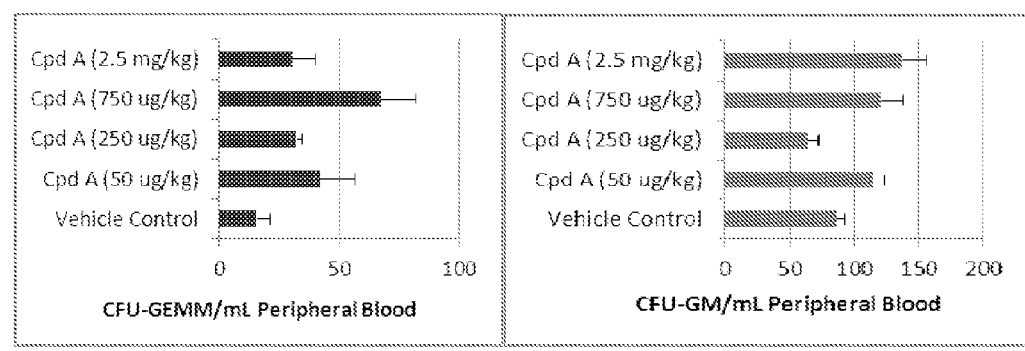
FIG. 4. Mobilization of CFU-GEMM and CFU-GM into peripheral blood after multiple subcutaneous injections of Compound A (dose response).

In the more extensive dose response experiment (Tabl.3 FIG. 4) it was shown that multiple injections of Compound A effectively mobilized CFU-GEMM in doses from 50 μg/kg up to 2.5 mg/kg with the best effect reached at 750 μg/kg of Compound C. Mobilization of more mature CFU-GM progenitors was not affected by Compound A injections.

TABLE 3

Mobilization of CFU-GEMM and CFU-GM after multiple subcutaneous injections of Compound A dose response.

| Treatment Group | CFU-GM | | CFU-GEMM | |
|---|---|---|---|---|
| | GM/ml blood | Fold Increase | GEMM/ml blood | Fold Increase |
| Vehicle Control | 85.8 | — | 15.4 | — |
| Compound A (50 μg/kg) | 114.8 | 1.3 | 42 | 2.7 |

TABLE 3-continued

Mobilization of CFU-GEMM and CFU-GM after multiple subcutaneous injections of Compound A dose response.

| Treatment Group | CFU-GM | | CFU-GEMM | |
| --- | --- | --- | --- | --- |
| | GM/ml blood | Fold Increase | GEMM/ml blood | Fold Increase |
| Compound A (250 µg/kg) | 64 | 0 | 32 | 2.1 |
| Compound A (750 µg/kg) | 120 | 1.4 | 67.2 | 4.4 |
| Compound A (2.5 mg/kg) | 136.8 | 1.6 | 30.4 | 2 |

Example 3

Effect of Sphingosine 1-Phosphate Gradient Disruption on Mobilization of Mouse Stem Cells from Bone Marrow into Peripheral Blood after Multiple Subcutaneous Injection of Compound A Sphingosine 1-phosphate (S1P) has many important roles in mammalian cells, including contributing to the control of cell survival and proliferation. It acts via five receptors (S1PR1-5) that couple to heterotrimeric G proteins. S1P possesses a chemoattractive property for a variety of cells and recently been implicated in stem cell mobilization. HSC egress from extramedullary tissues depends on S1P gradient. S1P was shown to regulate HSC AMD3100 and G-CSF-induced mobilization (Juarez J G, Harun N, Thien M, et al. Sphingosine-1-phosphate facilitates trafficking of hematopoietic stem cells and their mobilization by CXCR4 antagonists in mice. Blood. 2012; 119(3):707-716. Massberg S, Schaerli P, Knezevic-Maramica I, et al. Immunosurveillance by hematopoietic progenitor cells trafficking through blood, lymph, and peripheral tissues. Cell. 2007; 131(5):994-1008)

It has been reported recently that in vivo desensitization of S1P receptors by FTY720 or disruption of S1P gradient toward the blood, reduced steady state egress of immature progenitors and primitive stem cells (Golan e.a. 2012).

In this experiment the inhibitor of S1P lyase activity, 4-deoxypyridoxine (DOP, Sigma-Aldrich) was administrated to mice in the drinking water in order to test if disruption of S1P gradient has an effect on mobilization induced by Compound A.

Fifteen week-old DBA/2J male mice (Jackson Laboratories) were divided into 4 groups of 4 mice each. All Mice received glucose drinking water (10 g/L) throughout the duration of the study. DOP (30 mg/ml) was added to the glucose water of two groups. Mice were subcutaneously injected for four consecutive days with 500 µg/kg of Compound A or Saline. At one-hour post injections on day 4, peripheral blood from mice was harvested from the orbital plexus using capillary tubes (VWR) and collected into EDTA-containing tubes (BD). To determine mobilization of colony-forming unit cells out of the peripheral blood, mononuclear cells were plated in mouse methylcellulose complete media (R&D Systems).

The cells were placed into 35-mm Petri dishes at 100,000 cells per dish with 5 dishes per group. Cells incubated for 11 days in a 37° C. and 5% $CO_2$ humidified incubator. CFU colonies were then scored using an inverted microscope.

Figure 5:
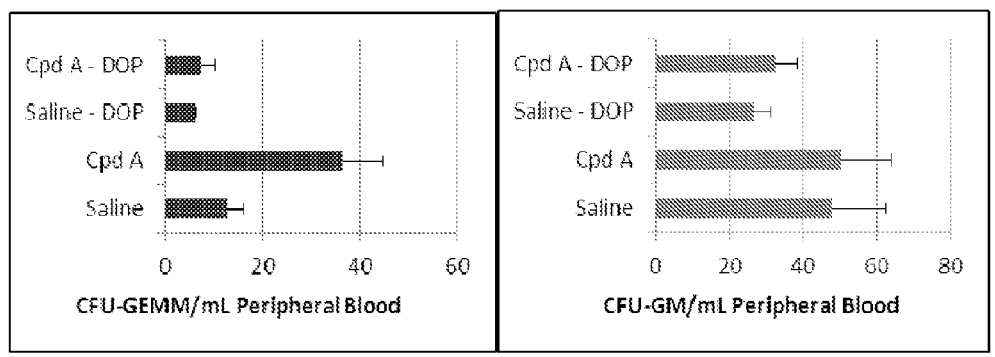
FIG. 5. S1P gradient regulates HSC mobilization and its disruption abrogates Compound A effect on CFU-GEMM egress into peripheral blood.

Results are presented on FIG. 5. S1P gradient disruption indeed decreased mobilization of colony forming cells into peripheral blood of mice treated with DOP (FIG. 5) as published by others (Golan et al. 2012, Juares et al. 2012). The Mobilizing effect of Compound A was completely abrogated by DOP treatment indicating S1P related mechanism of peptides.

We have previously established that stem cell mobilizing effect induced by Compound A is independent of SDF1-CXCR4 axis; now we have demonstrated that Compound A induced CFU-GEMM mobilization is dependent on S1P gradient.

Example 4

Angiogenesis Induced by bFGF in Matrigel Plugs is Stimulated by Multiple Subcutaneous Injections of Compound A Mobilization failure has been associated with older age, exposure to chemotherapeutic agents and especially with type II diabetes. Ferraro et al. (2011) recently reported that elevated blood glucose and glycated hemoglobin levels are more common in patients in whom HSCs failed to mobilize into the peripheral-blood system (Ferraro F, Lymperi S, Mendez-Ferrer S, et al. Diabetes impairs hematopoietic stem cell mobilization by altering niche function. Sci Transl Med 2011.) Poor stem cell mobilization and a reduction of the number of endothelial progenitor cells (EPCs) in type 2 diabetic patients prevent vasculogenesis and impair wound healing. Compound A by improving mobilization of stem cells may bring improvements to wound healing process.

During the proliferative phase of wound healing, neovascularization is indispensable for the generation of granulation tissue. Angiogenesis is also important in protection from tissue damage and the promotion of tissue repair. Matrigel plug assay allows to measure potential angiogenic effect of different compounds.

Figure 6:
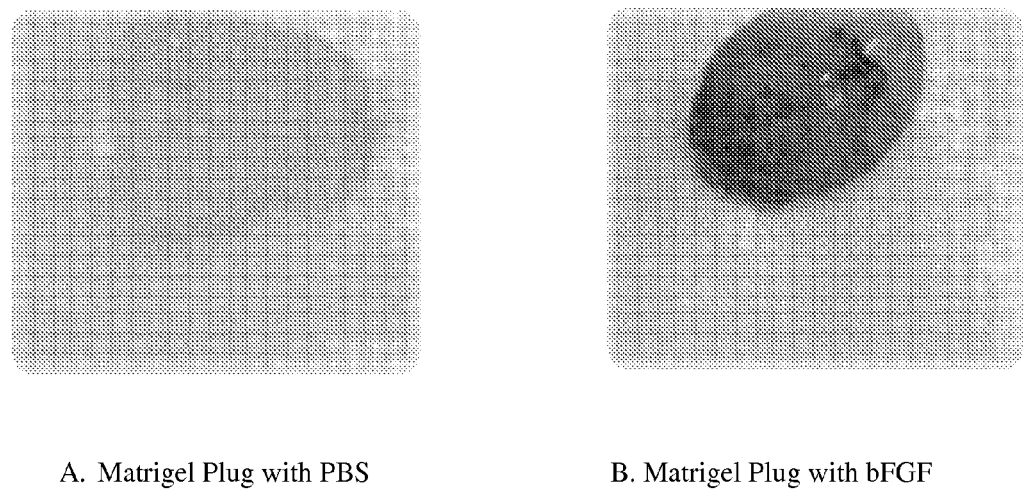
FIG. 6. Presence of human recombinant bFGF in Matrigel plug induces angiogenesis.

C57B1/6 mice were used in this experiment. Two Matrigel plugs were implanted under each mouse skin—one containing PBS and another 150 ng of bFGF. Three groups of mice were treated subcutaneously with 250 µg/kg of Compound A or 250 µg/kg of relevant peptide X or Saline daily for 7 days. Matrigel plugs were analyzed on day $8^{th}$ and hemoglobin (Hb) amount measured by Drabkin reagent. As shown on FIG. 6 there was no angiogenesis in PBS containing plugs, while bFGF promoted angiogenesis.

Figure 7:
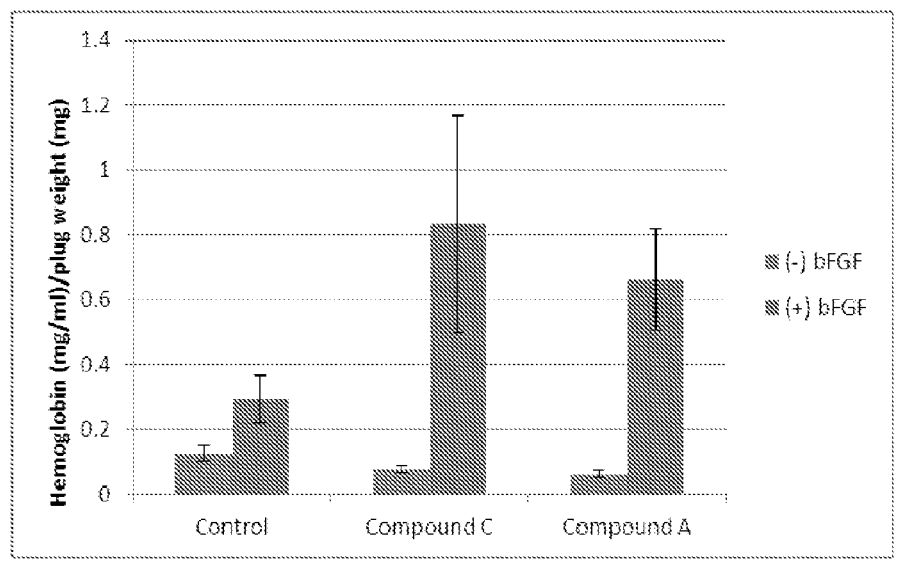
FIG. 7. Angiogenesis in Matrigel plugs after subcutaneous injections of peptides.

Hb content measurement is presented on FIG. 7. Both Compound A and related peptide Compound C had similar activity stimulating bFGF induced angiogenesis as compared with control mice receiving injections of Saline. Importantly, peptides did not have angiogenic activity themselves as far as no angiogenesis found in Matrigel plugs without bFGF (FIG. 7)

Figure 8:
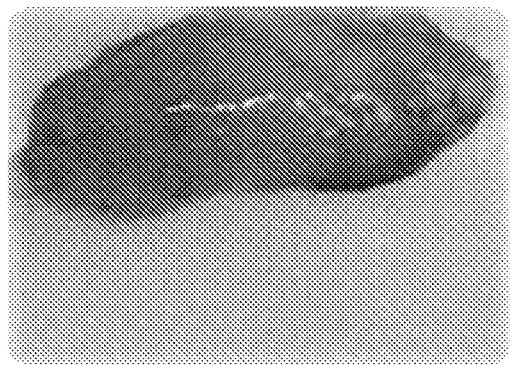
FIG. 8. Compound A effect on angiogenesis in db/db mice with diabetes in Matrigel Plugs.
Figure 8:
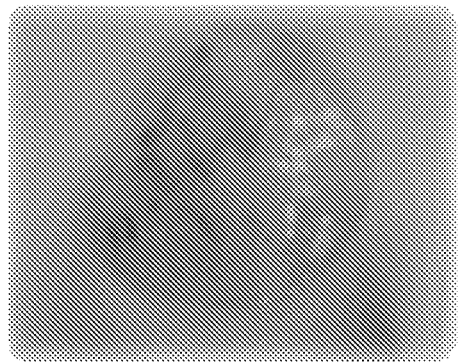
Figure 9:
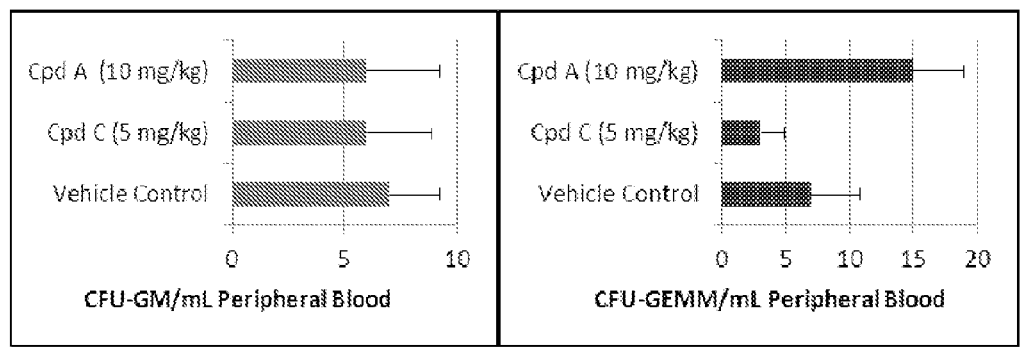
FIG. 9. Mobilization of CFU-GEMM and CFU-GM into peripheral blood after multiple subcutaneous injections of Compound A in db/db mice with high glucose level FIG. 10. TNF production by THP-1 cells in response to 20 ng/ml LPS FIG. 11. Compound A (10 nM) exerted a similar inhibitory effect on IL-8 production FIG. 12. Colony-forming units (CFU-GEMM) per 200 EML-Cl cells plated.

Next we used a type 2 diabetic mouse model (db/db), which recapitulates many diabetic phenotypes including poor tissue regeneration and wound healing. As seen on the pictures below, bFGF induced angiogenesis was also quite different in db/db mice as compared to non-diabetic C57BL6 mice; minimal angiogenic activity was detected in db/db mice on day 13, while there was substantial angiogenesis on day 9 in wild type mice. FIG. 8.

Example 5

Multiple Injection of Compound A in Wound Healing Model of Tissue Regeneration in Diabetes Mobilization studies on db/db mice with high glucose level in peripheral blood (>350 g/dL) mobilizing doses of the peptide Compound C were ineffective in such mice; even given at high dose 5 mg/kg subcutaneous injections did not cause CFU-GEMM mobilization. To test mobilizing effect of Compound A in db/db mice with high level of glucose the following experiment was conducted.

BKS.Cg-Dock7m+/+Leprdb/J male mice (10 weeks old Jackson Laboratories, stock #000642) were subcutaneously injected with 0.9% saline (vehicle control), 5 mg/kg Compound C, or 10 mg/kg Compound A (ThinkPeptides) for 5 consecutive days. At 7 days post initial injection, peripheral blood from 3 mice per group was harvested from the orbital plexus using capillary tubes (VWR) and collected into EDTA-containing tubes (BD).

Results obtained in this experiment indicate that treating db/db mice subcutaneously with a high dose of Compound C did not mobilize progenitor cells into the peripheral blood. Compound A at dose 10 mg/kg given subcutaneously over five consecutive days mobilized twice more CFU-GEMM into the peripheral blood of db/db mice than Saline control.

Effectiveness of subcutaneous injections of Compound A in mobilizing CFU-GEMM in db/db mice provides a functional advantage over Compound C, which is less active when administered by subcutaneous injection. Subcutaneous administration is more convenient for repeated treatments in the clinical setting of tissue revascularization and regeneration.

Example 6

Anti-Inflammatory Effect of Compound A

Excess inflammation is the major pathogenic mechanism for tissue damage and anti-inflammatory effects of potential drug candidates are important for successful tissue regeneration. N-acetyl-Ser-Asp-Lys-Pro (AcSDKP) (SEQ ID NO; 5), a tetrapeptide specifically degraded by angiotensin converting enzyme (ACE) is known to reduce inflammation (Sharma et. al. 2008).

AcSDKP was used as the positive control in this experiment to evaluate the potential anti-inflammatory effect of Compound A compared to related peptide Compound C.

THP-1 cells activated with 0.2 µM vitamin-D3 (EMD Biosciences Inc) and cultured in cRPMI [RPMI plus 10% ΔFBS (both Lonza)] were transferred to 24-well dishes. Different concentrations of Compound A or related peptides were added (in triplicate) and the plate placed in a 37° C. incubator.

After 1 hour, crude-LPS from E. coli 0111:B4 (20 ng-100 ng/ml final conc) was added to some wells. Supernatant aliquots were taken after 4 hours and cytokine levels determined using a cytokine bead array kit (BD558277).

Figure 10:
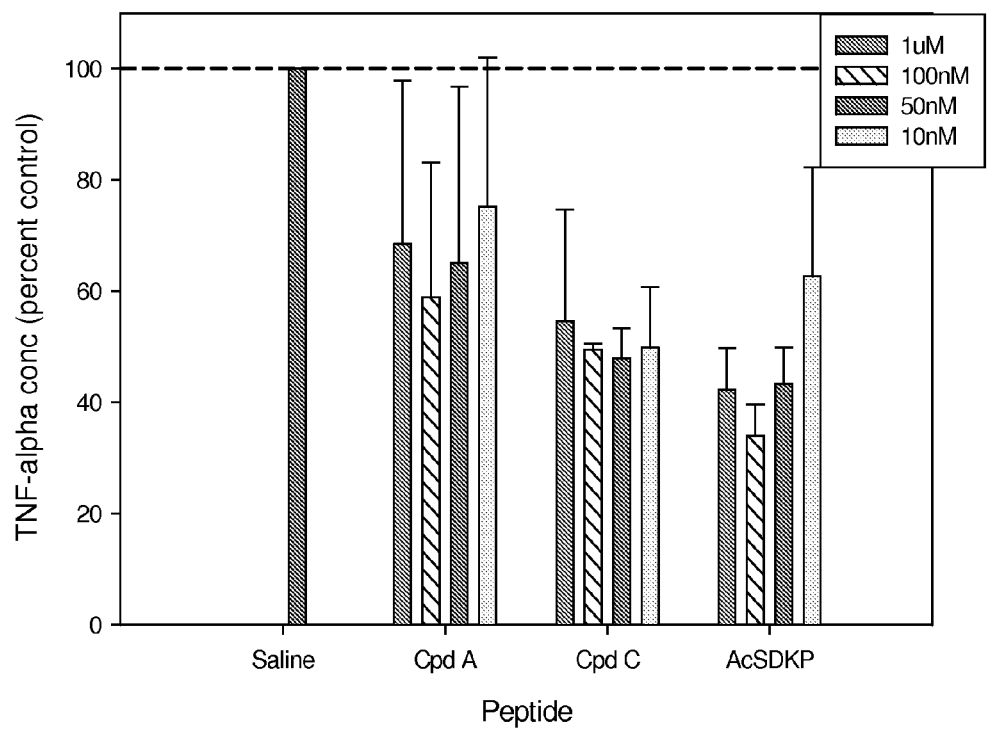
Figure 11:
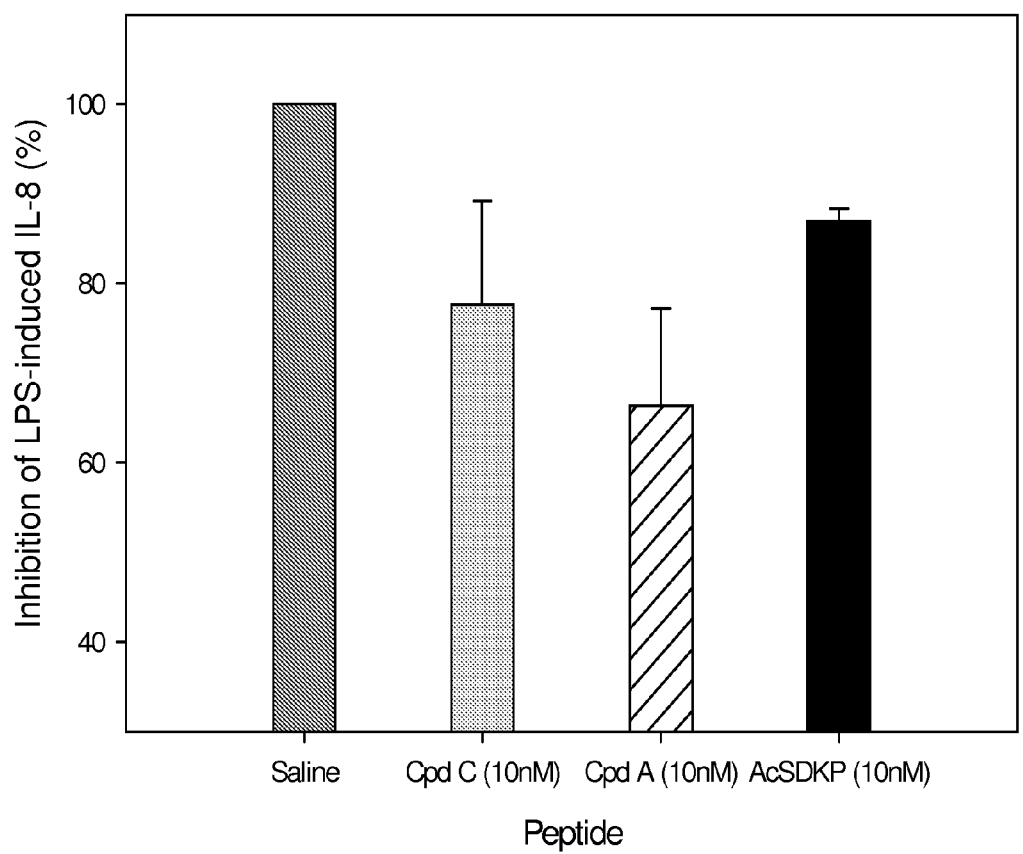

From FIG. 10, Ac-SDKP strongly inhibited TNFα secretion at levels ranging from 1 µM down to 10 nM. Compound A showed a more robust inhibition of TNFα secretion than AcSDKP or related peptide Compound C. The inhibition demonstrated by Compound A was maintained at the lowest level tested (10 nM).

Example 7

Antiapoptotic Effect of Compound A on Pluripotent Hematopoietic Stem Cells

Increased apoptosis is associated with tissue fibrosis, and its inhibition has been linked to the protection from fibrosis in several organs.

Erythroid myeloid lymphoid (EML) cells are an established multipotent hematopoietic precursor cell line (EML-Cl) that can be maintained in medium including stem cell factor (SCF) and Horse serum (HS). When plated in methylcellulose with cocktail of growth factors EML cells form mixed colonies (CFUmix or CFU-GEMM) containing a mix of erythroid and myeloid cells that can be enumerated after 7 days of incubation.

Starvation of EML-Cl cell line cells of serum and SCF during 3 hr causes majority of CFUmix to develop apoptosis and die, which decreases their number growing in methylcellulose substantially.

Presence of Compound A during starvation was able to rescue CFU-GEMM, providing both anti-apoptotic and growth promoting effects as shown in this example.

EML cells were grown in IMDM with 10% HS and 100 ng/ml of SCF in IMDM and used for all experiments in exponential growth phase.

Cells were washed from serum and growth factor with IMDM two times, counted and placed into 12 ml polypropylene tubes $2\times10^6$ cells in 2 ml for 3 hr incubation at t-37° C. and 5% CO2.

Cell suspensions after the incubation were centrifuged, diluted 5 times with IMDM and counted using a hemacytometer. Cells were adjusted to $10^3$ cells/mL in IMDM and cell suspension was placed into 50 mL tubes with 4.5 mL of Methylcellulose M3434 mixed well and seeded into 35-mm Petri dishes (Falcon BD351008) at 1 mL/dish. Cells were incubated at 37° C., 5% CO2.

CFU were scored using an inverted microscope after 7 days of incubation.

Figure 12:
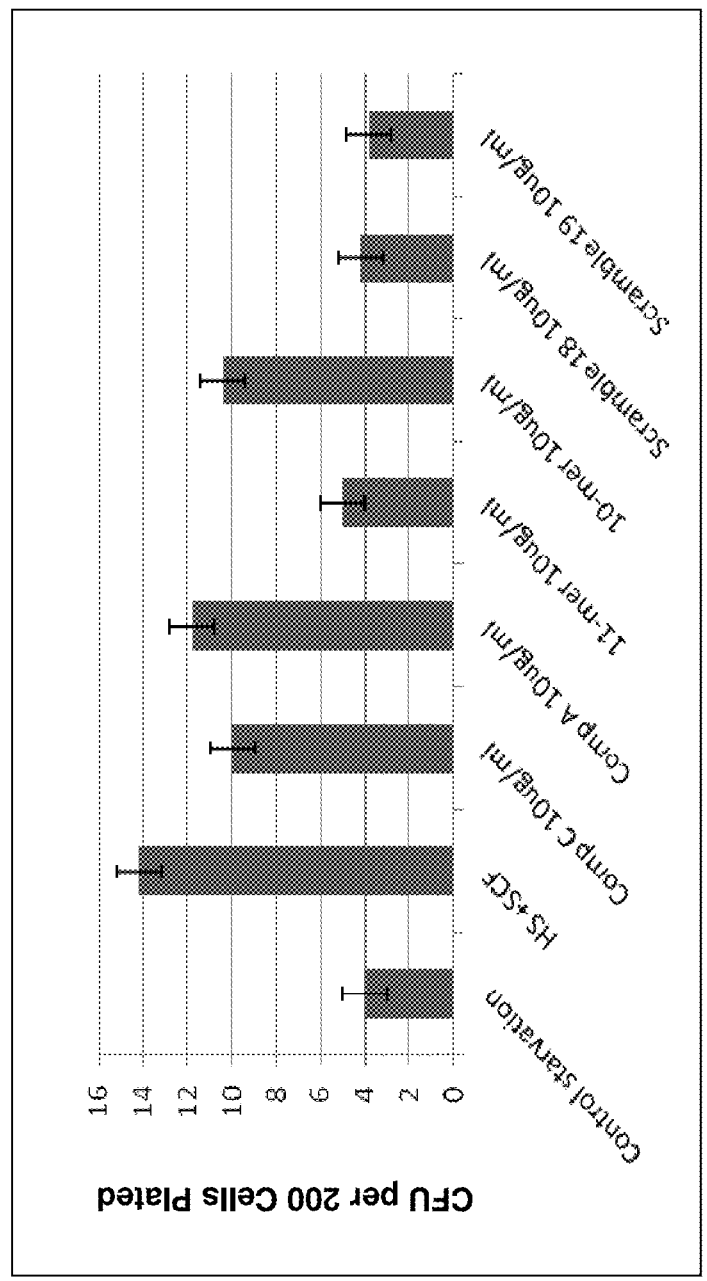

From previous experiments it was established that presence of HS alone or SCF alone did not rescue CFUmix, while presence of Compound A or related peptide Compound C rescued colony-forming cells similar to the effect of combined presence of HS and SCF (FIG. 12).

Because the EML cell line can be repeatedly cloned and has been derived from normal murine marrow it reflects the features of normal multipotential hematopoietic precursor cells. Thus, in vitro Compound A is a mitogen/survival factor able to induce growth regulation and modulate apoptosis among pluripotent hematopoietic stem cells it can also substitute SCF and HS synergistic signaling.

Survival of cells during serum and growth factor deprivation is dependent on level of executioner Caspase-3 activity.

To assess possible effect of Compound A and other peptides on Caspase-3 enzymatic activity during apoptosis induced by serum starvation fluorimetric assay Caspase-3 assay was performed according to the manufacturer's instructions (ApoAlert Clontech Mountain view CA).

Cell suspensions after the incubation were divided into two equal tubes (+/−Caspase inhibitor). Cells were centrifuged at 400×g for 5 min and re-suspend in chilled Cell Lysis Buffer with the following incubation on ice for 10 min., cell lysates were centrifugated in a microcentrifuge at max speed for 10 min at 4° C. and transferred into new tubes.

50 µl of 2× Reaction buffer/DTT mix and 1 µl of Caspase inhibitor added to 50 µl of cell lysate (+Inhibitor groups). 1 uL DMSO per 50 µL of 2× Reaction buffer was added to samples without inhibitor.

5 µL of the 1 mM Caspase-3 Substrate (DEVD-AFC; 50 µM final concentration) were added to each tube and incubated at t-37° C. for 1 hr in a water bath. All samples in duplicates were transferred to a 96 well plate. The plates were analyzed on a fluorescence plate reader (Spectramax Gemini.) at a 400 nm excitation and a 505 nm emission, and Caspase-3 activity was expressed relative to the medium control. Free AFC accumulation that resulted from cleavage of the asparatic-AFC bond monitored by fluorimeter and results in duplicates were recalculated according to the free AFC calibration curve.

Figure 13:
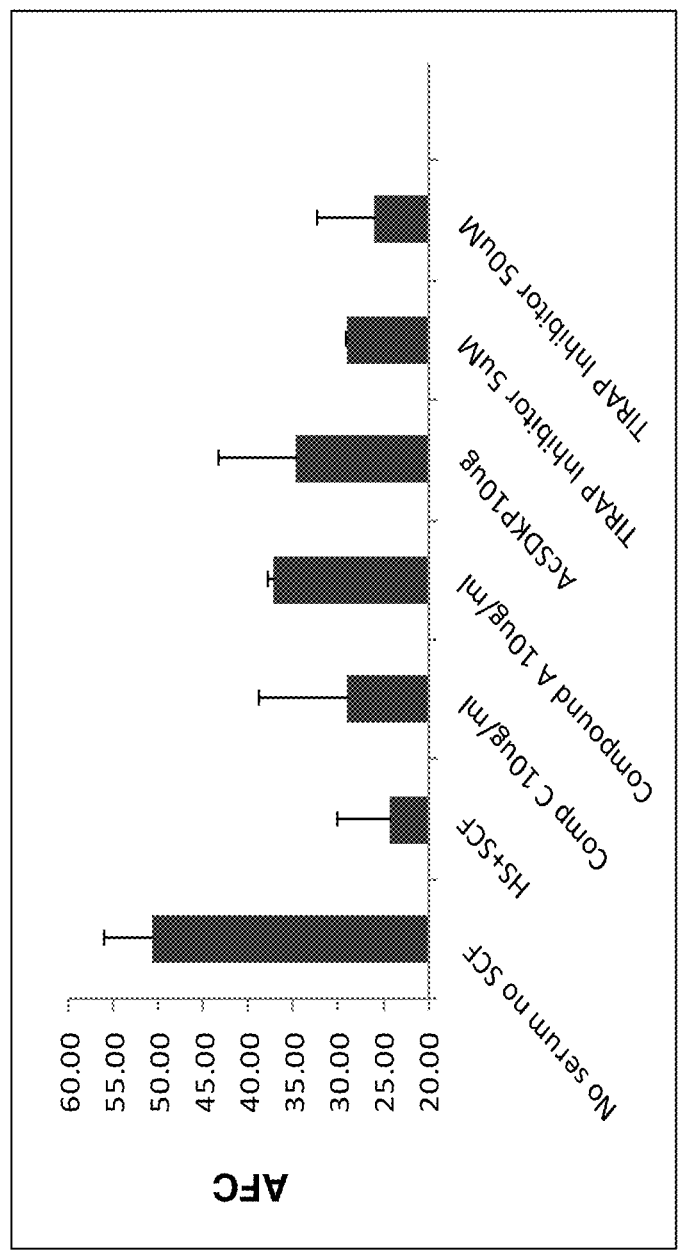
FIG. 13. Caspase-3 activity measured in relative units AFC in EML cell lysates after 3 hr of HS and SCF deprivation.

Caspase-3 activation induced by HS and SCF deprivation is shown in this experiment. Presence of all tested peptides Compound C, AcSDKP, Compound A during starvation prevented Caspase-3 activation (FIG. 13). Table 4 summarizes results of 3 identical experiments; in groups where Compound A, AcSDKP or Compound C were present during serum and SCF starvation caspase-3 activity was decreased down to the level found before "starvation".

TABLE 4

Inhibition of Caspase-3 proteolytic activity induced by HS and SCF deprivation by different peptides present during "starvation".

| Groups | Exp 1 | Exp 2 | Exp 3 | Sum of 3 experiments |
|---|---|---|---|---|
| Starvation control | 100% | 100% | 100% | 100% |
| No starvation (SCF + HS) | 70% | 81% | 50% | 67 +/− 15.7 |
| Starvation + Compound C 10 μM | 66% | 83% | 53% | 67.3 +/− 15 |
| Starvation + Compound A 10 μM | 73% | 89% | 64% | 75.3 +/− 12.6 |
| Starvation + AcSDKP 10 μM | 70% | 84% | 65% | 73 +/− 9.8 |

It has appeared that EML cells in absence of serum and stem cell factor undergo apoptosis via a caspase-dependent mechanism; presence of 10 μM of Compound A during serum and SCF starvation decreased Caspase-3 activity down to the level found in control EML cells (SCF+HS group).

It is of interest that pro-survival effect of Compound A was abrogated in presence of HS, but not delipidated HS (results are not shown), this may indicate that S1P presence in HS can interfere with Compound A effect. Serum deprivation changes S1P pathway drastically because serum contains from 200 nM to 1 μM of S1P.

It has been found previously by us that S1P, S1P1 receptor agonist SEW2871, S1P2 receptor antagonist JTE-013 or S1P3 antagonist CAY10444 used at 10 μM concentration rescued CFU-GEMM in this model similar to the effect of Compound A.

Figure 14:
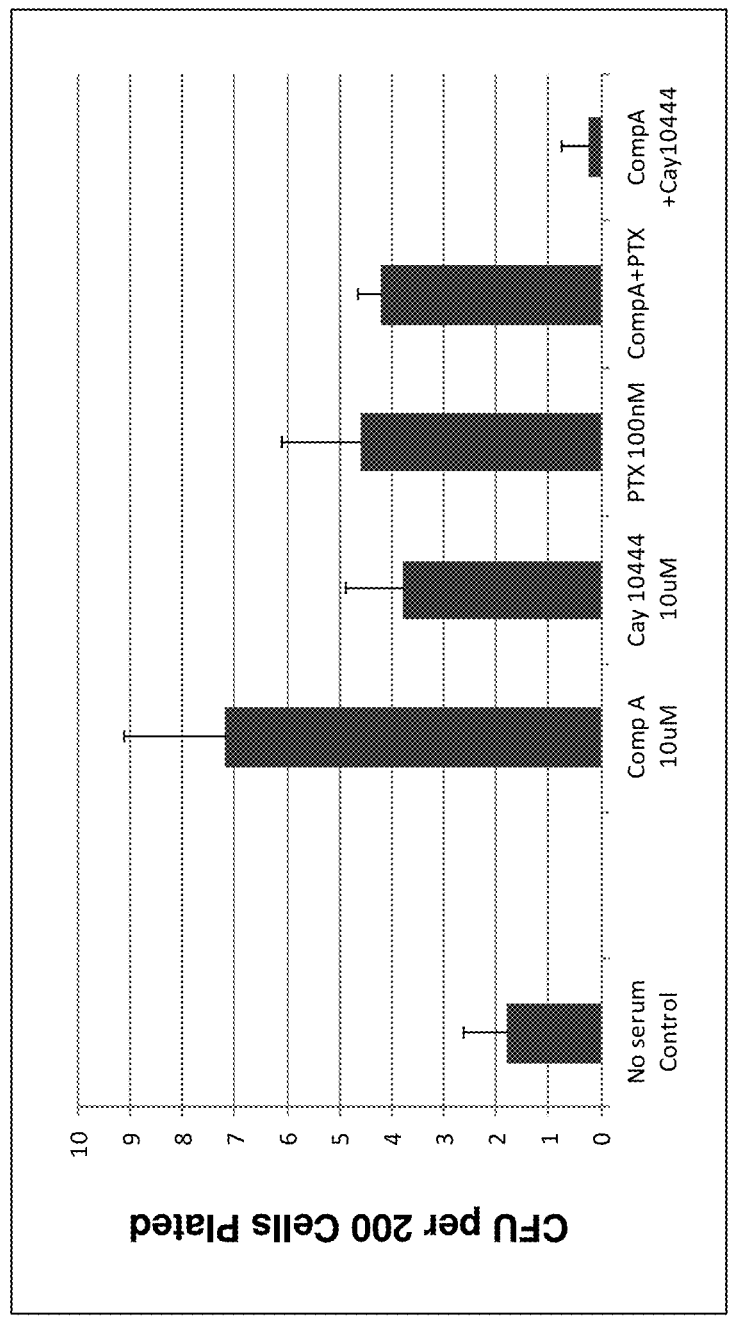
FIG. 14. CFU-GEMM number per 200 EML cells plated after 3 hr of serum and SCF deprivation; effect of Compound A and S1P3 receptor antagonist Cay 10444.

In this example combined effect of Compound A with S1P3 antagonists CAY 104444 was studied. S1P3 receptor antagonist CAY10444 abrogated pro-survival effect of Compound A (FIG. 14)

Figure 15:
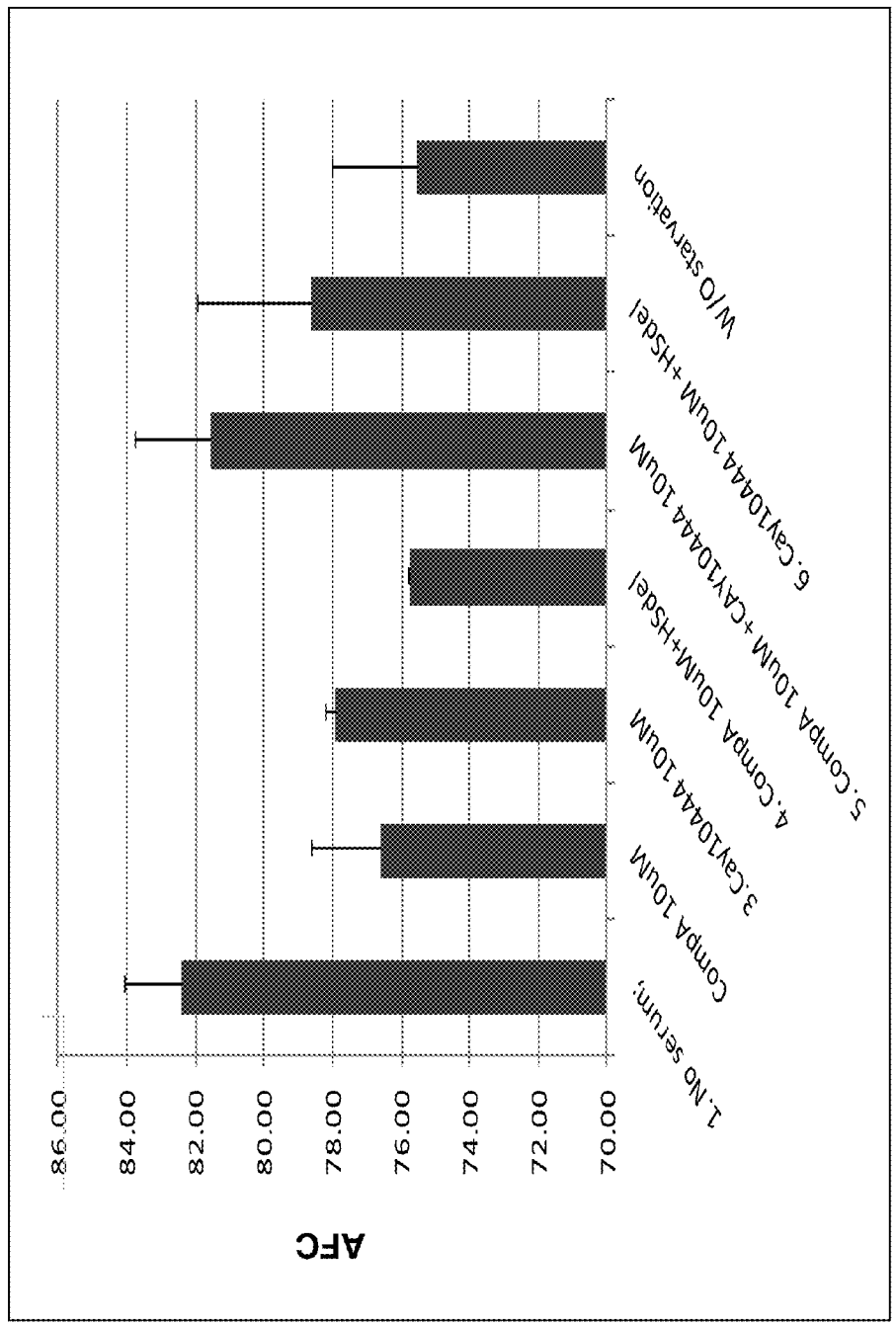
FIG. 15. Compound A effect decreasing Caspase-3 activity during serum starvation is abrogated by Cay 10444-S1P3 receptor antagonist.

The effect of Compound A decreasing proteolytic activity of Caspase-3 toward its substrate DEVD was also abrogated by co-incubation with CAY10444 (FIG. 15).

Example 8

Cleavage of N-Terminal Dipeptides During 3 hr Incubation with Bone Marrow Cells is Necessary for Compound a Activity Ac SDKP has very short half life and is rapidly cleaved by Angiotensin Converting Enzyme (ACE); N termini of peptides containing Xaa-Pro on the other hand are not easily cleaved by proteinases other than DPPIV, thus, the action of DPPIV is a rate-limiting step in degradation of peptides like Compound A. Other proteases can get involved only after DPPIV cleaves N-terminal dipeptide. Cathepsin G is involved in peptide metabolism its active site formed by the catalytic triad of Aspartate, Histidine and Serine hydrolyses a peptide bond after aromatic and strongly positively charged residues (F, K, R or L).

It was previously shown by us that N-terminal of the Compound A peptide can be hydrolyzed by human or murine recombinant DPPIV; we have also demonstrated that N-terminus acetylation prevented DPPIV cleavage (data not shown).

In this example we demonstrate cleavage of Compound A after 3 hr incubation of peptide with murine bone marrow cells.

B6D2F1 mice (HSD) were treated with 100 mg/kg testosterone propionate 24 hr before being sacrificed, femurs were removed and bone marrow cells (BMC) were flushed from bone marrow cavity. BMC—$5 \times 10^6$ cells/ml was resuspended in IMDM. Cell suspension was placed into 14-ml Falcon tubes (BD). Peptide Compound A, (Think Peptides) was added to cells at 100 μg/ml concentration. The appropriate volume of IMDM was added to another control supernatant tube containing 1 ml of cells. Cells were incubated for 3 hours at 37° C. After 3 hours of incubation, tubes were centrifuged, supernatants were collected and proteins with Mw>10 KD were eliminated by Amicon filtration at 3000 rpm 25 minutes. 0.5 ml of supernatant containing <10 Kd material was collected from each sample and heat inactivated during 10 min at t-70° C. The following samples were prepared for HPLC and MS: Control supernatant (<10 Kd); Supernatant from cells incubated with Compound A (<10 Kd); Compound A (50 μL) spiked into cell culture medium; and Compound C (50 μL) spiked into cell culture medium.

Figure 16:
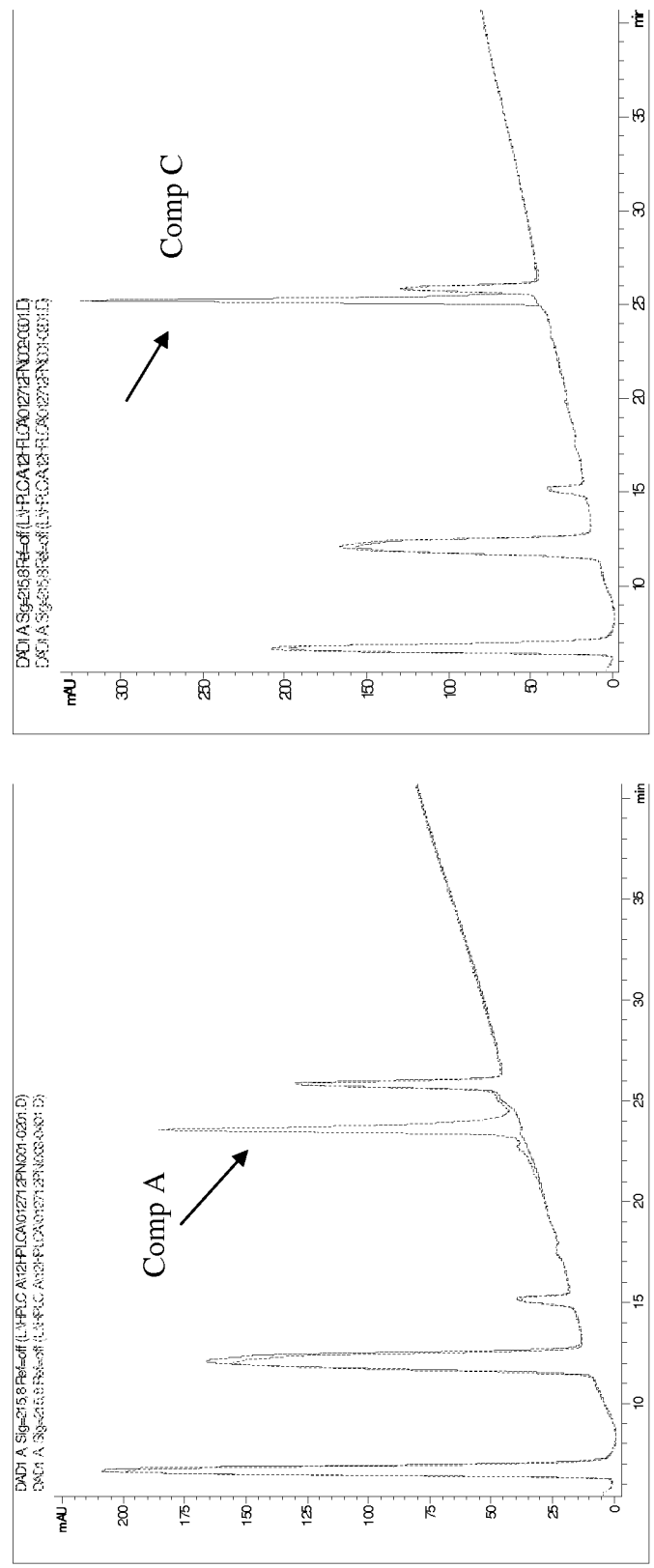
FIG. 16. HPLC histogram of Compound C and Compound A spiked in the medium.

HPLC histograms of Compound A or related peptide Compound C spiked into the medium are presented below (FIG. 16). Sequence analysis by MS confirmed the right sequences for both peptides clearly seen as two different peaks.

Figure 17:
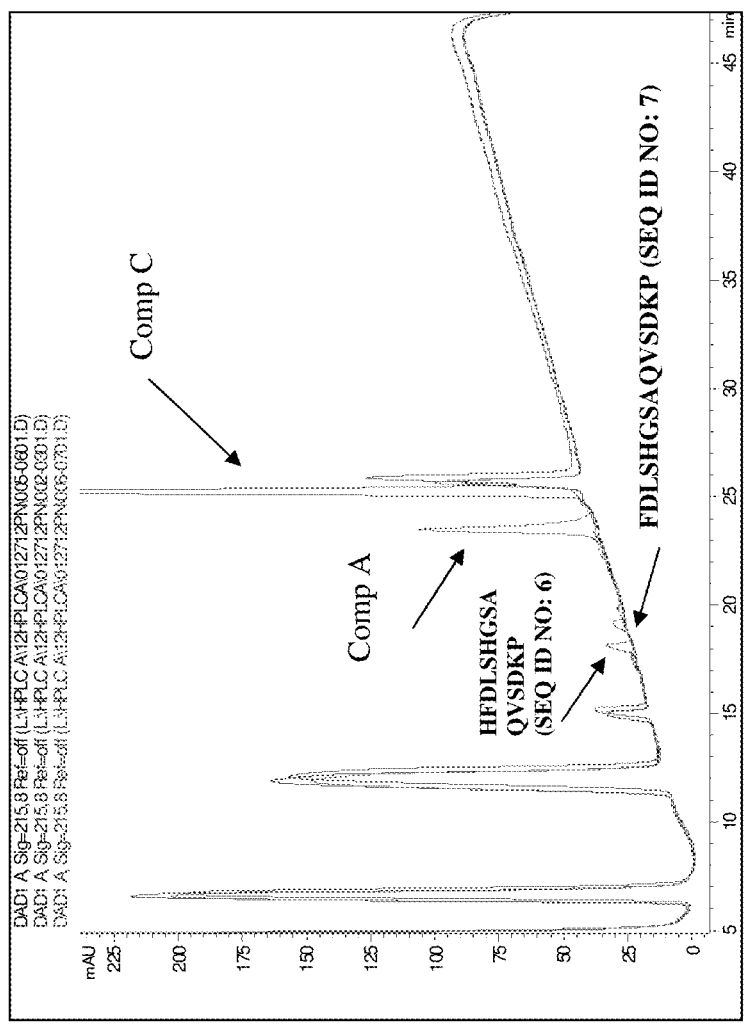
FIG. 17. Cleavage of Compound A after 3 hr incubation with murine bone marrow cells overlaid by Compound C spiked into medium; arrows show truncated Compound A peptides.

After 3 hr of incubation of Compound A with murine bone marrow cells in absence of serum as shown on HPLC histogram-proteolyses of the peptide was registered (FIG. 17)— two truncated peptides (Compound Ac shown by arrows) were formed. MS analysis detected HFDLSHGSAQVSDKP (SEQ ID NO: 6) and FDLSHGSAQVSDKP (SEQ ID NO: 7) products.

Example 9

Proliferation of Early Colony-Forming Stem Cells is Under Bidirectional Effect of Compound A Hyperproliferation of pluripotent stem cells is a major consequence of hematopoietic stress post-radiation or chemotherapy, part of the mechanism of autoimmune diseases as well as normal aging. It is also a major feature of diseases called Myelodisplastic Syndrome (MDS). While the phenotype of quiescent stem cells found under steady state conditions has been well defined, the phenotype of stem cells that proliferate yet retain the ability to engraft has not. However, such cells can be detected by their functional ability to grow a clone of pluripotent progenitors, colony-forming unit (CFU), able to differentiate into several types of hematopoietic cells—erythroid, granulocytic, macrophages forming a mixed colony CFU-Mix or CFU-GEMM.

This example shows that Compound A can both inhibit and stimulate proliferation of CFU-GEMM as measured by AraC "suicide" assay. Doses of Compound A acting on rapidly proliferating stem cells and decreasing their proliferation are about 2 logs lower than its stimulatory doses acting on slowly proliferating stem cell subset.

To determine if Compound A has the capacity to stimulate cycling of bone marrow stem cells in BDF1 mice several doses of Compound A were tested in stimulatory Ara C "suicide assay". Since the cells in S-phase during the 1-hour exposure to Ara-C are killed, the difference between the number of colonies in the sample not exposed to Ara-C and the number exposed to Ara-C, allows an estimation of the proportion of cells in S-phase in the bone marrow at the time of assay.

Bone marrow cells from naïve BDF1 male mice (Jackson Labs,) were incubated with Compound A (10 and 100 µg) in duplicate tubes for 3 hours at 37° C. After 3 hours of incubation, Ara-C (30 µg/ml) was added to 1 tube of cells and incubation was continued for an additional hour. After incubating, cells were washed and diluted in methylcellulose (Stem Cell Technologies) and seeded into 35-mm Petri dishes (1 ml/dish). Cells were incubated at 37° C., 5% $CO_2$. CFU-GEMM colonies were scored using an inverted microscope on day 7. Naïve mice have a low percentage of Ara-C kill during 1 hr incubation with cytotoxic drug, it has rapidly changed during the incubation with Compound A.

Figure 18:
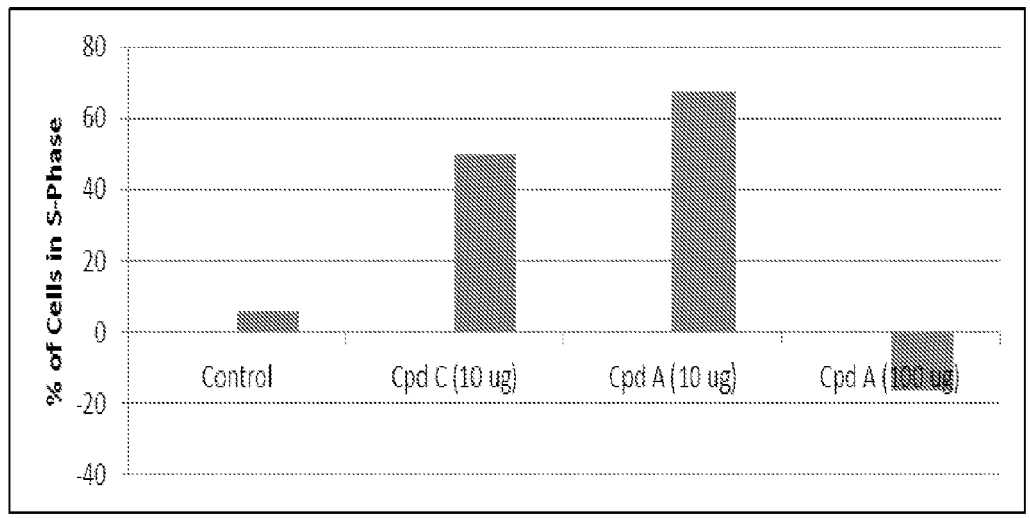
FIG. 18. Compound A increases percentage of CFU-GEMM in S-phase of cell cycle during four hours incubation with normal murine bone marrow cells.

As shown on FIG. 18, Co A at dose 10 µg/ml but not at 100 µg/ml increases percentage of CFU-GEMM in S-phase of cell cycle when incubated with murine bone marrow cells for 4 hr.

Alternatively, for the inhibitory AraC "suicide assay, BDF1 mice are injected (IP) with testosterone propionate (TSP) at 10 mg/100 g body weight 24 hours before initiation of cycling assay in order to activate proliferation of CFU-GEMM. 24 hr after TSP injection CFU-GEMM are proliferating substantially and more than 50% get killed by AraC during 1 hr incubation. Compound A in low doses inhibits CFU-GEMM proliferation and decreases percentage of cells killed by AraC in S-phase of cell cycle.

Figure 19:
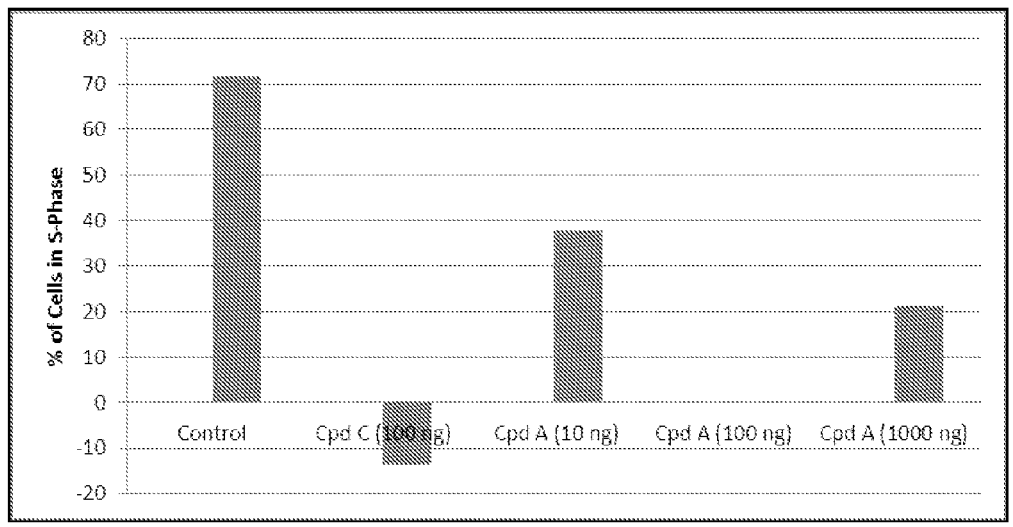
FIG. 19. Compound A decreases percentage of CFU-GEMM in S-phase of cell cycle during four hours incubation with testosterone stimulated murine bone marrow cells

Bone marrow cells from TSP treated BDF1 male mice (Jackson Labs) were incubated with different doses of peptides for 4 hr with AraC addition during the last 1 hr of incubation as for stimulatory assay. After incubating, cells were washed and diluted in methylcellulose (Stem Cell Technologies) and seeded into 35-mm Petri dishes (1 ml/dish). Cells were incubated at 37° C., 5% $CO_2$ for 7 days and CFU-GEMM colonies were scored using an inverted microscope. Results are presented in FIG. 19.

Similar to Compound C the presence of 100-1000 ng/ml of Compound A during 4 hr incubation of bone marrow cells brought down proliferation of HSC/HPC induced by in vivo testosterone injection. Thus, slow proliferating colony-forming cells from murine bone marrow will be activated by Compound A doses from 5-50 µg/ml while actively cycling CFU-GEMM from bone marrow of testosterone stimulated mice will be inhibited by doses between 100 and 1000 ng.

Our pharmacological strategy to improve mobilization and engraftment of HSC/HPC is based on doses of Compound A able to activate CFU-GEMM proliferation (from 5 to 50 µg/ml in vitro and from 50 µg/kg-10 mg/kg in vivo while "inhibitory doses" of Compound A 10-100 ng/ml in vitro and from 100 ng/kg-1 µg/kg in vivo are necessary for treatment and prophylaxis of MDS group of diseases, as maintenance after chemotherapy, irradiation and other events leading to hematopoietic stress.

Example 10

Effects of Subcutaneous Injections of Compound a on Hindlimb Ischemia in C57/BL6 Mice Ligation of the femoral artery in mice is an established model of hindlimb ischemia for testing treatments that might improve revascularization and functional recovery.

A total of 50 C57/B16 8-10 week old female mice were divided into 5 treatment groups (n=10/group).
Treatment groups included:
1. Vehicle Control
2. DFO (intramuscular) DFO (desferrioxamine) has been reported to improve revascularization by augmenting HIF-1α activation in sites of damage, to elicit secretion of local angiogenic factors and chemotactic signals that attract circulating repair-promoting stem and progenitor cells)
3. DFO (intramuscular)+Compound C (subcutaneous)
4. Compound A (subcutaneous)
5. DFO (intramuscular)+Compound A (subcutaneous)

TABLE 5

| Group | No. of Animals (M) | Time window | Treatment | |
|---|---|---|---|---|
| 1 | 10 | 14 Days | Vehicle PBS s/c. | 0.1 ml/10 g BW s.c. |
|   |   |   | PBS i.m. | 20 µl/10 g BW i.m. (4 sites) |
| 2 | 10 | 14 Days | Compound C s/c. | 0.1 ml/10 g BW s.c. |
|   |   |   | DFO i.m. | 20 µl/10 g BW i.m. (4 sites) |
| 3 | 10 | 14 Days | Compound A s/c | 0.1 ml/10 g BW s.c. |
|   |   |   | PBS i.m. | 20 µl/10 g BW i.m. (4 sites) |
| 4 | 10 | 14 Days | PBS s/c. | 0.1 ml/10 g BW s.c. |
|   |   |   | DFO i.m. | 20 µl/10 g BW i.m. (4 sites) |
| 5 | 10 | 14 Days | Compound A s/c | 0.1 ml/10 g BW s.c. |
|   |   |   | DFO i.m. | 20 µl/10 g BW i.m. (4 sites) |

Mice were subjected to unilateral total ligation and transection of the femoral artery under anesthesia (2% Isoflurane mixed with 100% oxygen). A unilateral incision was made over the left medial thigh of each mouse. The subcutaneous fat pad was cleaved for better exposure. The vein and nerve were separated from the femoral artery. The superficial femoral was ligated with 6-0 silk suture proximal to the caudally branching deep femoral artery and proximal to the branching of tibia arteries. The artery between the ligation points was excised. The connected branch from femoral artery was coagulated.

DFO or PBS control was immediately injected into adduct, quadriceps, gluteus and calf muscles after femoral artery excised. Each muscle received ¼ volume based on a total dose of 100 mg/kg DFO. After surgery, mice received intramuscular DFO every day for 14 days under brief anesthesia with 2% isoflurane on week days, and received intraperitoneal DFO on weekends.

Compound A in PBS, Compound C in PBS or Vehicle PBS were injected subcutaneously at 10 AM-11 AM on days 1 to 14 after surgery (day 0). Each mouse received a dose of 250 µg/kg subcutaneously.

Figure 20:
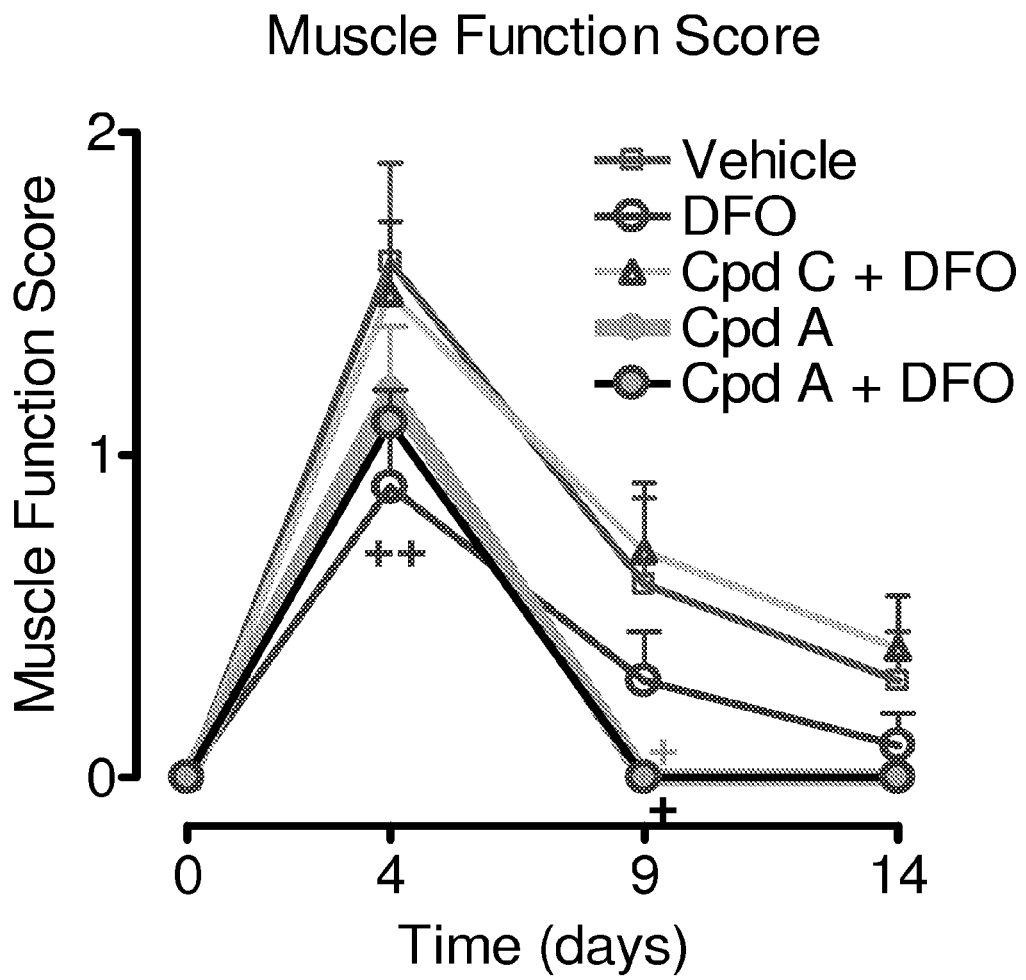
FIG. 20: Muscle function score in C57/BL6 mice with unilateral hind limb ischemia

On day 0, 4, 9, and 14, the condition of left hind limbs were evaluated with Muscle Function Score and Ischemia Score. All animal were fasted overnight before euthanization at which time plasma, adduct, calf tissues were collected on both left and right hind limbs. Each muscle were snap frozen in liquid nitrogen. Calf muscle was embedded with OCT and frozen in liquid nitrogen for histology analysis.
Muscle Function Score:
 0=normal toe and plantar flexion;
 1=no toe but plantar flexion;
 2=no toe and plantar flexion;
 3=dragging foot.
Ischemia Score:
 0=normal;
 1=cyanosis or loss of nail(s);
 2=partial or complete loss of digit(s);
 3=dry necrosis beyond digits into front part of foot.
Results:
 Unilateral hindlimb ischemia caused impairment of muscle function. By day 9, mice (n=10/group) treated with Compound A or Compound A+DFO displayed near-normal function as evaluated by the Muscle Function Score (FIG. 20); other groups maintained impairment at day 9 (DFO) and at day 14 (Vehicle Control and Compound C+DFO).

Figure 21:
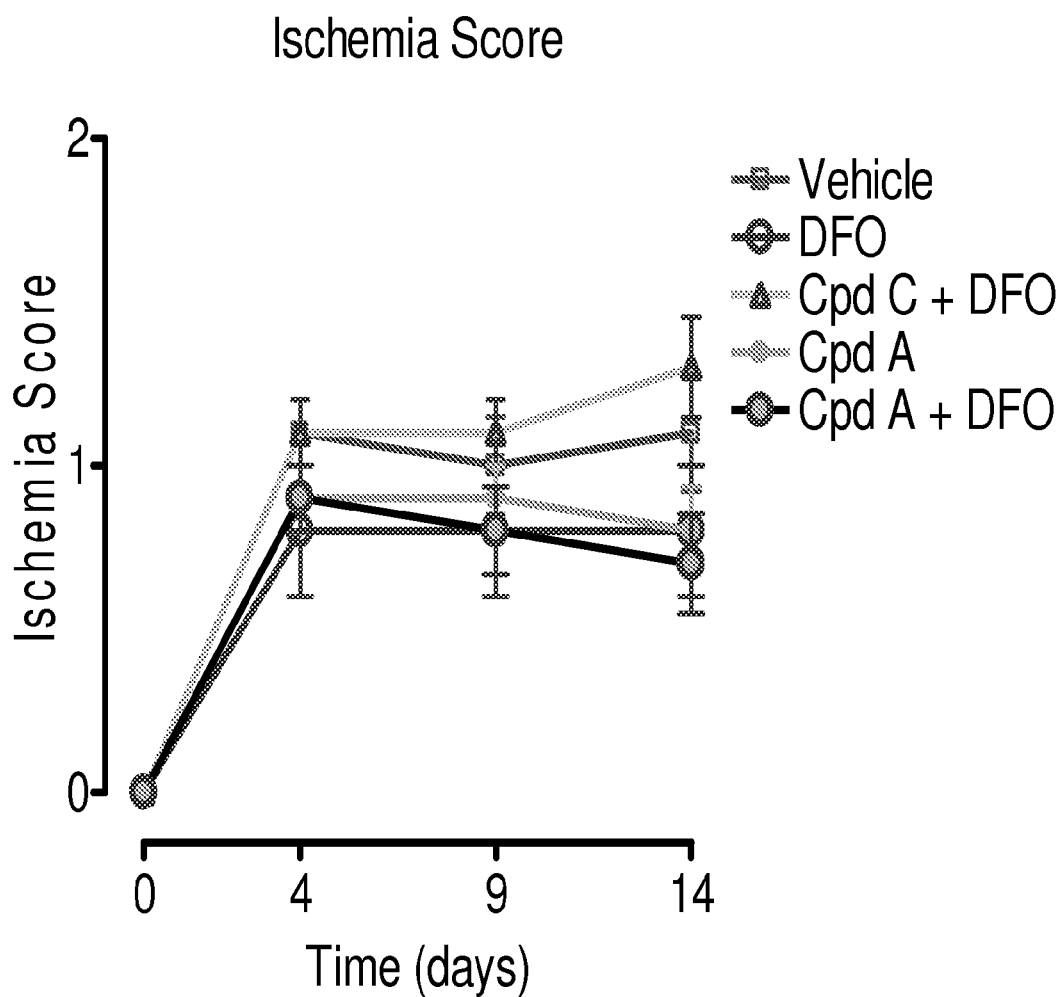
FIG. 21: Ischemia Score in C57/BL6 mice subjected to unilateral femoral artery ligation

Mice (n=10/group) treated with subcutaneous Compound A and Compound A+DFO also displayed less impairment than Vehicle-treated mice on the Ischemia Score (FIG. 21).

Figure 22:
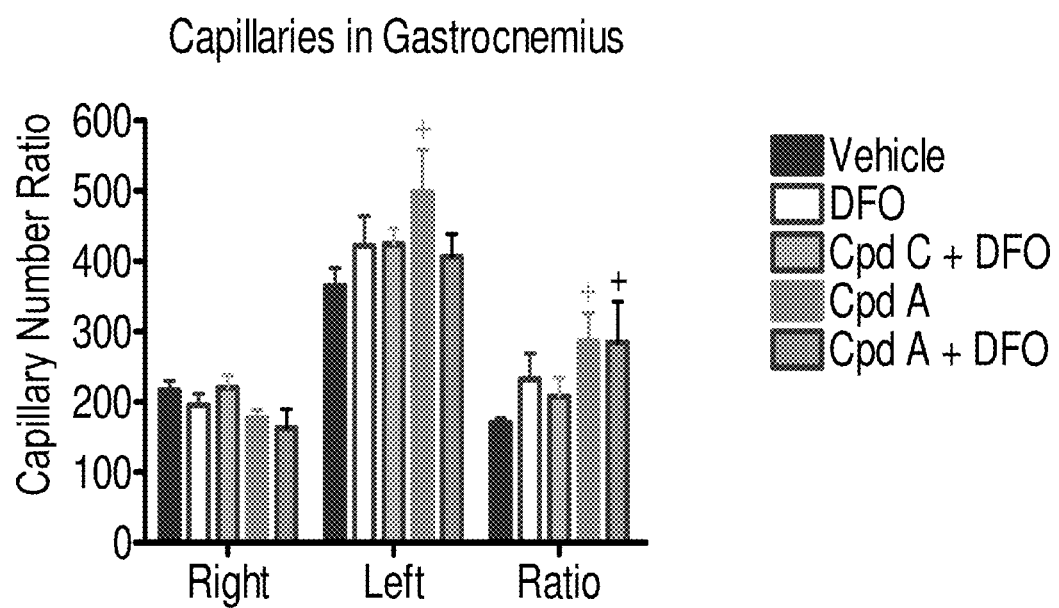
FIG. 22: Capillary counts in gastrocnemius muscle sections in mice subjected to unilateral (left) hind limb ischemia

Recovery of circulation and function in the hindlimb ischemia model involves angiogenesis and revascularization, a process triggered by oxygen deficits. Revascularization was evaluated on day 14 after artery ligation by counting capillaries in cross sectional histology slides prepared from gastrocnemius muscles from both legs. In all groups including vehicle controls, capillary counts were higher in the left (ischemic) muscle than in the right, indicating compensatory revascularization. The ratio of capillary numbers in the left versus right legs were higher in the mice treated with Compound A (n=5) and Compound A+DFO (n=5) mice than in the other treatment groups (n=10) (FIG. 22).

CONCLUSION

Subcutaneous administration of Compound A improved function, ischemic damage, and capillary counts in C57/BL6 mice subjected to unilateral hindlimb ischemia.

What is claimed is:

1. An oligopeptide having the sequence Phe-Xaa-His-Phe-Asp-Leu-Ser-His-Gly-Ser-Ala-Gln-Val-Ser-Asp-Lys-Pro (SEQ ID NO: 1), wherein Xaa is Pro or Ala.

2. The oligopeptide of claim 1 having the sequence Phe-Pro-His-Phe-Asp-Leu-Ser-His-Gly-Ser-Ala-Gln-Val-Ser-Asp-Lys-Pro (SEQ ID NO: 2).

3. The oligopeptide of claim 1 having the sequence Phe-Ala-His-Phe-Asp-Leu-Ser-His-Gly-Ser-Ala-Gln-Val-Ser-Asp-Lys-Pro (SEQ ID NO: 3).

4. A pharmaceutical composition comprising a compound (SEQ ID NO: 1) for mobilizing stem cells from bone marrow of a subject.

5. A method of mobilizing stem cells from bone marrow of a subject, comprising administering to the subject an amount of compound (SEQ ID NO: 1) effective to mobilize the stem cells.

6. The method of claim 5, wherein the subject is a human and the amount of (SEQ ID NO: 1) is from 100 micrograms to 10 milligrams per administration, administered from 1 time per week to 3 times per day.

7. A method for treating a subject in need of one or more of preservation, repair, or regeneration of bodily tissue, or revascularization, comprising the method of claim 5, thereby promoting the one or more of preservation, repair, or regeneration of bodily tissue or regeneration in the subject.

8. A method for treating a subject in need of one or more of preservation, repair, or regeneration of bodily tissue, or revascularization, comprising the method of claim 6, thereby promoting the one or more of preservation, repair, or regeneration of bodily tissue or regeneration in the subject.

9. The method of claim 7, wherein the tissue that is preserved, repaired or regenerated is pancreatic tissue.

10. A method of treating diabetes comprising the method of claim 9.

11. The method of claim 8, wherein the tissue that is preserved, repaired or regenerated is pancreatic tissue.

12. A method for treating diabetes comprising the method of claim 11.

13. The method of claim 7, wherein the tissue that is preserved, repaired, or regenerated is dermal tissue.

14. A method for treating a dermal wound, comprising the method of claim 13.

15. The method of claim 8, wherein the tissue that is preserved, repaired or regenerated is dermal tissue.

16. A method of treating a dermal wound, comprising the method of claim 15.

17. The method according to claim 5, wherein the compound has the sequence Phe-Pro-His-Phe-Asp-Leu-Ser-His-Gly-Ser-Ala-Gln-Val-Ser-Asp-Lys-Pro (SEQ ID NO: 2).

18. The method according to claim 5, wherein the compound has the sequence Phe-Ala-His-Phe-Asp-Leu-Ser-His-Gly-Ser-Ala-Gln-Val-Ser-Asp-Lys-Pro (SEQ ID NO: 3).

* * * * *